(12) United States Patent
Hermanussen et al.

(10) Patent No.: US 6,701,915 B1
(45) Date of Patent: Mar. 9, 2004

(54) DEVICE FOR INHALING MEDICAMENTS USING SUPPORTED PRESSURE RESPIRATION

(76) Inventors: Michael Hermanussen, Aschauhof 3, D-24340, Altenhof (DE); Karl-Heinz Rolli, Murgstrasse 9, D-68753, Waghäusel (DE)

( * ) Notice: Subject to any disclaimer, the term of this patent is extended or adjusted under 35 U.S.C. 154(b) by 0 days.

(21) Appl. No.: 10/130,614

(22) PCT Filed: Nov. 20, 2000

(86) PCT No.: PCT/EP00/11512

§ 371 (c)(1), (2), (4) Date: May 17, 2002

(87) PCT Pub. No.: WO01/37910

PCT Pub. Date: May 31, 2001

(30) Foreign Application Priority Data

Nov. 20, 1999  (DE) .......................... 199 55 902

(51) Int. Cl.⁷ ............................................. A61M 11/00
(52) U.S. Cl. ............................. 128/200.22; 128/203.28; 128/205.15
(58) Field of Search ........................ 128/203.12, 203.14, 128/203.28, 205.15, 200.22

(56) References Cited

U.S. PATENT DOCUMENTS

| | | | | |
|---|---|---|---|---|
| 2,208,633 A | * | 7/1940 | Heidbrink ............... | 128/203.28 |
| 2,284,964 A | * | 6/1942 | Mautz et al. ........... | 128/205.12 |
| 2,582,210 A | * | 1/1952 | Stanton .................. | 417/390 |
| 3,123,071 A | * | 3/1964 | Felts ...................... | 128/203.12 |
| RE25,871 E | * | 10/1965 | Andreasen ............. | 128/204.28 |
| 3,291,121 A | * | 12/1966 | Vizneau .................. | 128/205.15 |
| 3,291,122 A | * | 12/1966 | Engstrom et al. ...... | 128/200.16 |
| 3,307,542 A | * | 3/1967 | Andreasen ............. | 128/204.28 |
| 4,409,977 A | * | 10/1983 | Bisera et al. ........... | 128/205.15 |
| 4,691,700 A | * | 9/1987 | Brychta et al. ......... | 128/200.21 |
| 4,790,305 A | * | 12/1988 | Zoltan et al. ........... | 128/200.23 |
| 4,928,683 A | * | 5/1990 | Westerkamp et al. .. | 128/203.12 |
| 4,932,401 A | * | 6/1990 | Perkins .................. | 128/203.12 |
| 5,320,093 A | * | 6/1994 | Raemer .................. | 128/203.12 |
| 5,398,675 A | * | 3/1995 | Henkin et al. .......... | 128/203.12 |
| 5,505,236 A | * | 4/1996 | Grabenkort et al. ... | 141/329 |
| 5,507,280 A | * | 4/1996 | Henkin et al. .......... | 128/203.12 |
| 5,509,406 A | * | 4/1996 | Kock et al. ............. | 128/203.14 |
| 5,647,352 A | * | 7/1997 | Niemi et al. ............ | 128/204.28 |
| 6,340,023 B2 | * | 1/2002 | Elkins .................... | 128/200.21 |
| 6,349,723 B1 | * | 2/2002 | Kock ...................... | 128/203.28 |
| 6,463,929 B1 | * | 10/2002 | Scheuch et al. ........ | 128/203.15 |

FOREIGN PATENT DOCUMENTS

GB  2 104 394  3/1983

* cited by examiner

*Primary Examiner*—Aaron J. Lewis
(74) *Attorney, Agent, or Firm*—Herbert Dubno

(57) ABSTRACT

The inventions relates to a small light device (1) for inhaling medicaments using supported pressure respiration, comprising a mouthpiece (2), a reservoir (5; 12), which has a variable volume for receiving respiratory gas and which can be connected to the mouthpiece (2) and into the flow either directly or using a distributor (3), an adjustable, gas-tight closer (8) between the mouthpiece (2) and the reservoir (5; 12) and at least one connecting element (10; 17) for the medicament supply to the reservoir, (5; 12), said medicament being supplied either directly or indirectly, using a distributor (3). The reservoir (5; 12) has a wall which adjusts to its change in volume. Said wall can be expanded against a restoring force by the pressurised influx of respiratory gas, in such a way that the supported pressure respiration take place using the effect of the restoring force during inhalation of the respiratory gas which contains the medicament.

7 Claims, 2 Drawing Sheets

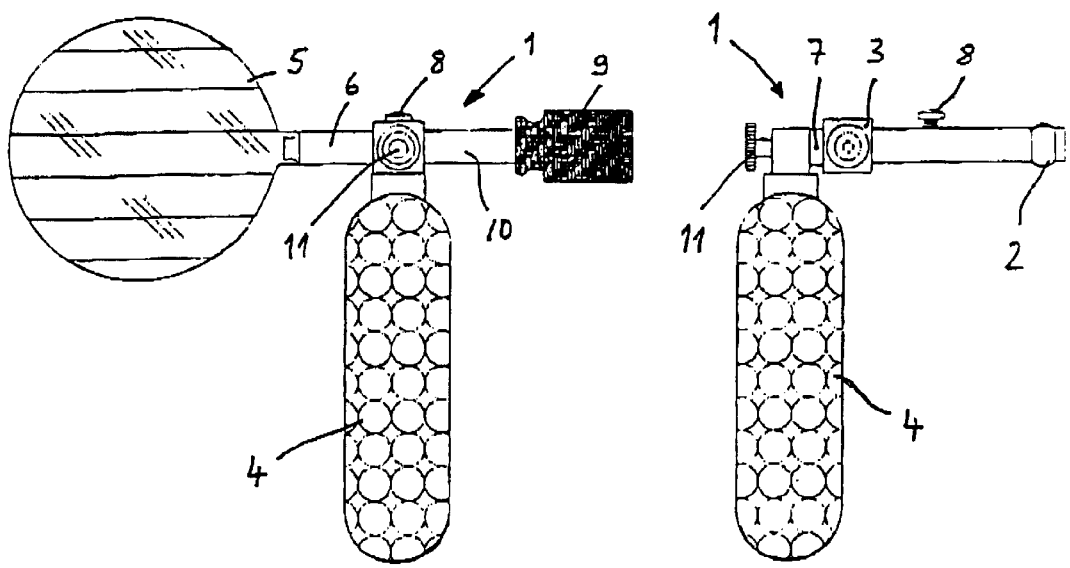
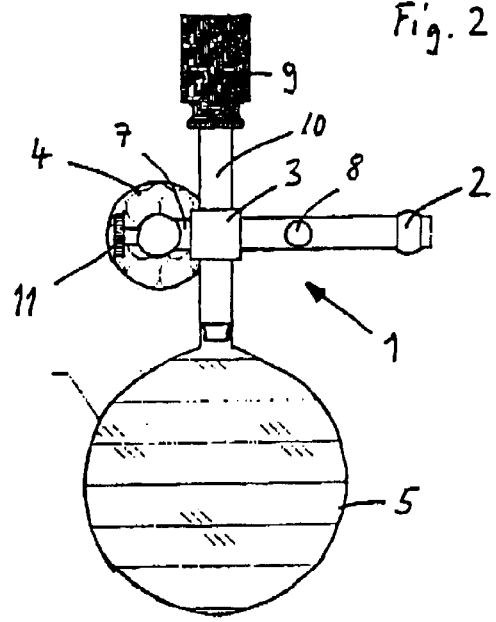

DEVICE FOR INHALING MEDICAMENTS USING SUPPORTED PRESSURE RESPIRATION

CROSS REFERENCE TO RELATED APPLICATIONS

This application is a national stage of PCT application PCT/EP00/11512 filed Nov. 20, 2000 and is based upon German national application 19955902.3 filed Nov. 20, 1999 under the International Convention.

FIELD OF THE INVENTION

The invention relates to a device for inhaling pharmaceutical drugs by means of auxiliary positive-pressure respiration.

BACKGROUND OF THE INVENTION

During normal spontaneous human breathing, inhalation occurs as the respiratory muscles actively expand the thorax, thereby creating a pressure gradient, with the result that air is drawn in, i.e. flows into the lungs in accordance with the pressure gradient. Exhaling occurs passively in that a pressure rise takes place in the lung as the thorax is restored elastically to its default position, with the result that the consumed air is expelled from the thorax and the lungs. The mean pressure level by means of which inhalation and exhalation occur alternately corresponds to the atmospheric pressure.

Under conditions of illness or disease, e.g. in the case of asthma, small and medium-sized respiratory tracts (bronchial tubes) in the lungs can become constricted. The flow resistance in them increases, particularly during exhalation, with the result that the patient is forced to work actively by means of his muscles even during exhalation. As a consequence an additional pressure increase occurs in the thorax which can result in a complete collapse of the constricted respiratory tracts and it becomes impossible to expel air from the relevant sections of the lungs (i.e. air is trapped). Such situations often occur in the form of attacks and can be acutely life-threatening for the patient (acute asthma attack).

Devices with which the patient can inhale pharmaceutical drugs himself are known in the art. These pharmaceutical drugs are generally introduced into the respiratory tracts via the mouth as an aerosol or powder inhalant by means of a nebulizer or atomizer. An advantageous embodiment has retarding chambers, such as spacers, in which a particular volume of air is enriched with aerosol or powder inhalant before being inhaled and then is made available for inhalation. This improves the effectiveness of the inhaled pharmaceutical drugs. The disadvantage of such simple, easily portable, non-electrically operated inhalation systems that can be used by the patient himself in an emergency is that they can only be operated at atmospheric pressure. Lung sections which cannot take part in spontaneous breathing because of the above-described collapse of small respiratory tracts therefore remain inaccessible at atmospheric pressure even during emergency treatment with inhaled pharmaceutical drugs.

Respiration under positive pressure is known in the art. Such methods are applied in particular in breathing apparatus used in a non-breathable atmosphere and by divers. The disadvantage of such methods is that they are not designed for patients suffering from acute breathing difficulties and are also complex, requiring valves, tubing and also, if appropriate, as with breathing apparatus with a closed breathing circuit and diving equipment, a carbon dioxide absorber to process the exhaled air which is rich in carbon dioxide. The standard positive-pressure respiration system for treating patients with severe breathing difficulties is generally in the form of complex, fixed respirators in hospital areas designed for this purpose and proceeds either automatically (mechanical respiration without action by the patient) or in assisted mode (with action by the patient), or—if the patient is breathing spontaneously—also via CPAP (continuous positive airway pressure). Respiration can be carried out with positive pressure either continuously or intermittently. Simple, non-electrically-operated manual devices for this purpose are not known in the art.

OBJECT OF THE ART

It is the object of this invention to provide a very simple, small, portable, easily operated, integrated, self-contained device which is independent of electrical power and is suitable in particular for asthmatics and patients with other obstructive lung diseases for temporarily improving the inhalation of pharmaceutical drugs which efficiently combines the therapeutic effect of inhaled pharmaceutical drugs, the advantages of a retarding chamber and the physical effect of positive-pressure respiration for a brief period, i.e. for the limited period of acute breathing difficulties.

SUMMARY OF THE INVENTION

In accordance with the invention a very simple, small, portable, easily operated, integrated and self-contained device is provided which can comfortably be stored in a bag, e.g. a handbag. The device consists of a closed system into which the patient can exhale without a breathing air circuit being created. By contrast with the complex respirators which operated hitherto with a closed breathing circuit and at a pressure greater than atmospheric pressure, there is no need here for the valves and tubing. Similarly, no processing of the exhaled gas, e.g. in a carbon dioxide absorber, takes place, meaning that a device in accordance with the invention is limited to a few minutes of use, i.e. to the duration of the acute breathing difficulties, because of the accumulation of carbon dioxide.

The device comprises a mouthpiece which can be fully encompassed by the lips; a reservoir which has a variable volume to accommodate inhalant gas, can be connected to the mouthpiece in the direction of flow either directly or via a distributor and provides the characteristic features of a retarding chamber; an adjustable airtight closure between the mouthpiece and the reservoir; and at least one connection for the pharmaceutical drug feed in the form of an aerosol or powder inhalant to the reservoir, with the pharmaceutical drug feed being either direct or indirect via a distributor. An essential feature is that the reservoir has a variable wall to enable it to change its volume, where said wall can be expanded under the pressure of inflowing inhalant gas against a restoring force such that, as a result of the action of the restoring force, auxiliary positive-pressure respiration occurs when the inhalant gas containing the pharmaceutical drug is inhaled.

The variable wall of the reservoir can be embodied in various ways so that it is at least partially movable, for example being formed of a combination of rigid and movable sections. In accordance with a preferred embodiment the variable wall has at least one elastic wall and an elastic balloon in particular forms the reservoir.

A further variant provides for the reservoir to have at least one rigid wall section on which a distributor and/or at least one connection for the mouthpiece, the inhalant gas filler connection or the pharmaceutical drug feed are provided.

A preferred embodiment provides for a gas reservoir with a compression-proof wall containing compressed inhalant gas to be connected to the reservoir directly or indirectly via a distributor and for a reclosable valve to be configured between the gas reservoir and the reservoir. In this device the gas reservoir is filled when in transport mode, and the reservoir, which is preferably in the form of a balloon with a floppy elastic wall, is empty. In accordance with the invention the pharmaceutical drugs are inhaled by first opening the filled gas reservoir with a compression-proof wall by means of a valve, allowing oxygen or oxygen-rich air to flow into the elastic-walled reservoir. As soon as the elastic-walled reservoir is sufficiently full, the valve between the gas reservoir with a compression-proof wall and the elastic-walled reservoir can be closed again, for example by the user. This means that, as in a balloon, the pressure in the elastic-walled reservoir is slightly higher than atmospheric pressure, at between greater than 0 and approx. 30 cm water column. This is caused by the elastic wall tension of the reservoir. Pharmaceutical drugs which act on the respiratory tracts can now be introduced into the elastic-walled reservoir, which thus takes on the function of a retarding chamber, from at least one commercially available bottle for the spray inhalation of pharmaceutical drugs. The device is now ready for use and can be used by the patient.

The patient encompasses the mouthpiece firmly with his lips, then either fits a nose clip or actively blocks his palate to prevent the physiological route for air through the nose, and then opens the airtight closure between the mouthpiece and the elastic-walled reservoir by pressing with his finger or by means of a device which automatically opens the closure when the patient first inhales. The increased pressure in the elastic-walled reservoir is also transferred to the patient's lungs via the respiratory tracts, thereby allowing oxygen and pharmaceutical drugs to enter the patient's lungs until the pressure gradient between the elastic-walled reservoir and the lungs has equalized. In this process oxygen and pharmaceutical drugs are also forced into those sections of the lungs which were inaccessible as a result of constricted and previously collapsed respiratory tracts at atmospheric pressure.

The lungs are therefore pre-inflated for the period that the device in accordance with the invention is in use, and the pressure in them corresponds no longer to atmospheric pressure but to the pressure set by the elasticity of the reservoir wall or by a spring device in the case of reservoir wall elements which can slide over each other. Continued inhalation and exhalation occurs, as in the case of the previous spontaneous breathing at atmospheric pressure, by alternate active muscular expansion and elastic contraction of the thorax. This counteracts the collapse of the small respiratory tracts which occurs as a result of disease and also enables those lung sections to be treated by means of inhalation which were inaccessible, i.e. were not reached by spontaneous breathing, at atmospheric pressure.

Because the patient draws inhalant gas and pharmaceutical drugs from a closed system into which he exhales again without processing of the exhaled gas, oxygen is consumed, and the carbon dioxide level is enriched. Because of the latter feature in particular, the patient must cease inhalation with the device in accordance with the invention after a short period within which the state of acute breathing difficulty should have improved.

If pharmaceutical drugs need to be inhaled again by means of auxiliary positive-pressure respiration, the consumed inhalant gas is discharged from the reservoir via the closure and the mouthpiece, and the gas reservoir is opened again via the valve. The process as described above is then repeated.

The volume and elasticity or restoration properties of the reservoir can be individually adjusted by selecting an appropriate balloon or restoration device such as a spring.

If it is decided to dispense with multiple use of the device in accordance with the invention and instead to use it only for single-use emergency treatment, the gas reservoir with a compression-proof wall in a further advantageous embodiment of the invention with improved handling only needs to contain oxygen for a single use. This enables the device to be designed such that it is even smaller and lighter, and it is also possible to dispense with a reclosable valve between the gas reservoir with a compression-proof wall and the reservoir with a variable wall. In this case, however, a new gas reservoir must be fitted before each new use.

The central functional element of the invention is the reservoir with a variable or at least partially elastic wall which is both responsible for the respiration pressure and also, like a retarding chamber, delivers a certain volume of inhalant gas which is enriched with aerosol or powder inhalant before being inhaled. Various practical embodiments of the invention are possible; in particular, the various elements of the device in accordance with the invention can either be connected separately to a central distributor or, like a set of bagpipes, the mouthpiece and the connections for the gas reservoir with a compression-proof wall and the bottles for the spray inhalation of pharmaceutical drugs can open directly into the elastic-walled reservoir.

BRIEF DESCRIPTION OF THE DRAWING

Embodiments of the device in accordance with the invention are described below with reference to the drawings in which:

FIG. 1 is a schematic front view of a first embodiment of a device for inhaling pharmaceutical drugs in accordance with the invention;

FIG. 2 is a side view of the inhalation device;

FIG. 3 is a view of the inhalation device; and

SPECIFIC DESCRIPTION

Figure 4:
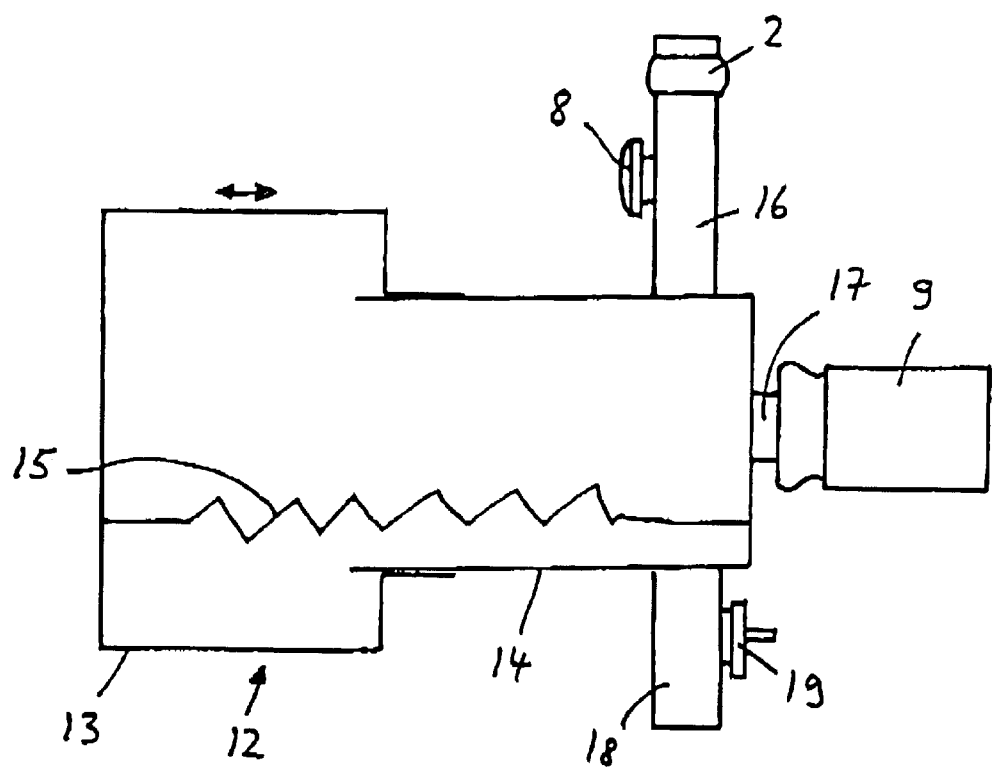
FIG. 4 is a schematic side view of a second embodiment of a device in accordance with the invention.

A first embodiment of a device 1 for improved inhalation of pharmaceutical drugs by means of auxiliary positive-pressure respiration comprises a mouthpiece 2 and a distributor 3 to which the mouthpiece 2 is connected. An adjustable, airtight closure 8 is provided between the mouthpiece 2 and the distributor 3. A gas reservoir 4 with a compression-proof wall and a reservoir 5 with an elastic wall and variable volume, for example a balloon, are mounted on separate connections 6 and 7, respectively, of the distributor 3. The reservoir 5 can also take the form of a concertina with an internal tension spring (not shown), which acts on the concertina to reduce its volume. Compressed inhalant gas can flow out of the gas reservoir 4 by means of a valve 11 on the connection 7 and then through the distributor 3 into the reservoir 5, thereby increasing the volume of the latter against the elastic force of the wall of the reservoir 5.

A commercially available bottle 9 for the spray inhalation of pharmaceutical drugs is mounted on a separate connection 10 of the distributor 3. The pharmaceutical drug can be introduced in the form of an aerosol or powder inhalant from the bottle 9, e.g. at the press of a finger, via the distributor 3 into the reservoir 5, which acts like a retarding chamber.

The mouthpiece 2 and the distributor 3 are preferably made of easily cleaned plastic. The gas reservoir 4 with a compression-proof wall can be a standard pressurized-gas bottle which preferably contains at least one or a plurality of inhalant gas doses for the reservoir 5 or the balloon.

If, in a variant of the device according to the invention, a distributor 3 is dispensed with, the mouthpiece 2 is connected to the adjustable, airtight closure 8, and the gas reservoir 4 with a compression-proof wall and at least one commercially available bottle 9 for the spray inhalation of pharmaceutical drugs is connected directly to the elastic-walled reservoir 5 (not shown) by means of separate connections. In either case there is a duct connecting the mouthpiece 2 and the reservoir 4, 5 so that curing active breathing of a person using the device the flow path therebetween is unrestricted.

The operation of the device 1 for the improved inhalation of pharmaceutical drugs by means of auxiliary positive-pressure respiration without a distributor corresponds in principle to that of the variant with a distributor.

In a device (not shown) which has been modified by comparison with the above-described device 1, the distributor 3 contains only three connections for the mouthpiece 3, the bottle 9 and the reservoir 5, with the fourth connection 7 having been omitted. The inhalant gas used to support inhalation by means of positive pressure is introduced into the reservoir 5 by connecting the latter to and filling it from an inhalant gas source, e.g. an inhalant gas bottle or an inhalant gas connection in a laboratory. The reservoir 5 is then connected to the connection 6 of the distributor 3, the pharmaceutical drug is introduced into the reservoir 5 from the bottle 9, and the inhalant gas containing the pharmaceutical drug can be inhaled via the mouthpiece 2 after the closure 8 has been opened. If a balloon is used as the reservoir 5, the elastic balloon connection is attached to the inhalant gas source and, after filling, is temporarily closed by squeezing the neck as with a standard play balloon, until the balloon connection has been attached to the connection 6 of the distributor 3.

A further embodiment of the device shown in FIG. 4 contains a reservoir 12 with a wall enclosing the variable volume made of two solid, telescopable—e.g. cylindrical—wall elements 13 and 14 which are pre-tensioned to reduce the volume of the reservoir 12 by means of, for example, a tension spring 15 mounted inside the reservoir 12. The mouthpiece 2 is directly connected to the wall element 14 of the reservoir 12 via a connection pipe 16 which contains a closure 8 that is operated manually or automatically when the patient inhales for the first time. Furthermore, the wall element 14 contains a connection 17 for the bottle 9 containing a pharmaceutical drug and a filler connection 18 for inhalant gas on which a locking valve 19 is mounted.

In this device the reservoir 12 therefore comprises a wall made of rigid wall elements, though said wall elements form an elastic wall with reference to the variable volume because of the elastic restoring force of the tension spring 15.

To prepare the device for inhalation, the inhalant gas filler connection 18 is connected to an inhalant gas source, and the reservoir 12 is filled with pressurized inhalant gas, during which the two wall elements 13 and 14 move relative to each other against the force of the tension spring to increase the volume. Once the required volume of inhalant gas has flowed into the reservoir 12, the locking valve 19 is closed, and the reservoir 12 is removed from the inhalant gas source. After the pharmaceutical drug has been introduced into the reservoir 12 from the bottle 9, the device is ready for inhalation.

The mutual movement of the two wall elements 13 and 14 to increase the volume is limited by means of, for example, a stop. A pressure relief valve can be provided in the wall of the reservoir 12 to avoid exceeding the maximum permissible inhalant gas pressure when filling the reservoir 12 with inhalant gas.

To provide a larger inhalant gas volume of approx. 3–4 liter for this device, an unfoldable, airtight, elastically extendable or non-extendable bag or similar can be attached to the slidable wall element 13. When not in use, this bag remains folded away and therefore small; when the device is in use, it can be unfolded and filled with inhalant gas. If the volume change as a result of the movable wall element is insufficient for positive-pressure support for inhalation, the elastic, balloon-like bag can provide the additional assistance.

What is claimed is:

1. A device for inhaling pharmaceutical drugs by means of auxiliary positive-pressure respiration, comprising:
   a mouthpiece;
   a reservoir having a variable volume to accommodate inhalant gas and connected to the mouthpiece;
   an adjustable, airtight closure between the mouthpiece and the reservoir and at least one connection for feeding a pharmaceutical drug to the reservoir, said reservoir having a variable wall to change its volume which can be extended by inflowing pressurized inhalant gas acting against a restoring force, with the result that there is positive-pressure assistance when the inhalant gas containing the pharmaceutical drug is inhaled because of the action of the restoring force, the reservoir having at least one rigid wall section, to which at least one of a distributor, a connection for the mouthpiece, an inhalant gas filler connection and the pharmaceutical drug feed is attached, the reservoir having at least two wall elements which can move over each other, can be displaced relative to each other to increase the volume and are elastically pre-tensioned against a sliding motion to increase the volume by a spring device.

2. A device for inhaling pharmaceutical drugs by means of auxiliary positive-pressure respiration, comprising:
   a mouthpiece;
   a reservoir having a variable volume to accommodate inhalant gas and connected to the mouthpiece;
   an adjustable, airtight closure between the mouthpiece and the reservoir and at least one connection for feeding a pharmaceutical drug to the reservoir, said reservoir having a variable wall to change its volume which can be extended by inflowing pressurized inhalant gas acting against a restoring force, with the result that there is positive-pressure assistance when the inhalant gas containing the pharmaceutical drug is inhaled because of the action of the restoring force, the reservoir having a lockable inhalant gas filler connection, and an elastic wall at a filler opening of the reservoir.

3. A device for inhaling pharmaceutical drugs by means of auxiliary positive-pressure respiration, comprising:
   a mouthpiece;
   a reservoir having a variable volume to accommodate inhalant gas and connected to the mouthpiece;

an adjustable, airtight closure between the mouthpiece and the reservoir and at least one connection for feeding a pharmaceutical drug to the reservoir, said reservoir having a variable wall to change its volume which can be extended by inflowing pressurized inhalant gas acting against a restoring force, with the result that there is positive-pressure assistance when the inhalant gas containing the pharmaceutical drug is inhaled because of the action of the restoring force; and a three-way distributor to connect the mouthpiece, the reservoir and the pharmaceutical drug feed or a four-way distributor to connect the mouthpiece, variable volume reservoir, the pharmaceutical drug feed and a gas reservoir.

4. A device for inhaling pharmaceutical drugs by means of auxiliary positive-pressure respiration, comprising:

a mouthpiece;

a reservoir having a variable volume to accommodate inhalant gas and connected to the mouthpiece;

an adjustable, airtight closure between the mouthpiece and the reservoir and at least one connection for feeding a pharmaceutical drug to the reservoir, said reservoir having a variable wall to change its volume which can be extended by inflowing pressurized inhalant gas acting against a restoring force, with the result that there is positive-pressure assistance when the inhalant gas containing the pharmaceutical drug is inhaled because of the action of the restoring force; and a duct forming an unobstructed pathway for both inhaled gas and exhaled gas between said mouthpiece and said reservoir during active breathing by a person using said device such that during the active breathing a flow path between the mouthpiece, the reservoir and the duct is unobstructed and inhaling and exhaling controls the flow therethrough exclusively.

5. The device defined in claim 4 wherein a pressurized gas vessel having rigid walls is connected to said duct.

6. The device defined in claim 5 wherein said reservoir is a balloon.

7. The device defined in claim 5 wherein said reservoir has two telescoping parts elastically pretensioned against a sliding motion by a spring.

\* \* \* \* \*